United States Patent [19]
Clarke et al.

[11] Patent Number: 5,987,094
[45] Date of Patent: Nov. 16, 1999

[54] COMPUTER-ASSISTED METHOD AND APPARATUS FOR THE DETECTION OF LUNG NODULES

[75] Inventors: Laurence P. Clarke, Temple Terrace; Wei Qian, Wesley Chapel; Fei Mao, Tampa, all of Fla.

[73] Assignee: University of South Florida, Tampa, Fla.

[21] Appl. No.: 08/960,815

[22] Filed: Oct. 30, 1997

Related U.S. Application Data

[60] Provisional application No. 60/029,335, Oct. 30, 1996.
[51] Int. Cl.⁶ .................................................... G01N 23/04
[52] U.S. Cl. .............................. 378/62; 382/128; 382/132
[58] Field of Search ........................ 378/62, 98; 382/132, 382/128

[56] References Cited

U.S. PATENT DOCUMENTS

| | | | |
|---|---|---|---|
| 5,365,429 | 11/1994 | Carman | 378/37 |
| 5,598,481 | 1/1997 | Nishikawa et al. | 382/130 |
| 5,668,888 | 9/1997 | Doi et al. | 382/132 |

OTHER PUBLICATIONS

Fei Mao, Wei Qian and Laurence P. Clarke, Fractional Dimension Filtering for Multiscale Lung Nodule Detection, SPIE vol. 3034, Feb. 1997, pp. 449–454.

Fei Mao, Wei Qian and Laurence P. Clarke, 1.5 Dimensional Circular Pattern Filter for Multiscale Lung Nodule Detection, EMBS96: Final Program & Abstract Book, Nov. 1996.

*Primary Examiner*—David Vernon Bruce
*Attorney, Agent, or Firm*—Allen, Dyer, Doppelt, Milbrath & Gilchrist, P.A.

[57] ABSTRACT

A computer-assisted diagnostic (CAD) method and apparatus are described for the enhancement, detection, and classification of suspicious regions in digital x-ray images, with particular emphasis on lung nodule detection using chest x-ray images. An objective is to improve the sensitivity and specificity of detection of suspicious areas such as nodules, while maintaining a low false positive detection rate. A modular CAD technique has been developed to be potentially automatic and to be used as a second-opinion method for lung nodule detection. The method consists of using a plurality of CAD modules to preprocess and enhance image features, including image preprocessing, selective enhancement, segmentation, and feature extraction using a multiresolution/multiorientation wavelet transform and a computationally efficient filter, a 1.5 D circular pattern filter.

30 Claims, 11 Drawing Sheets

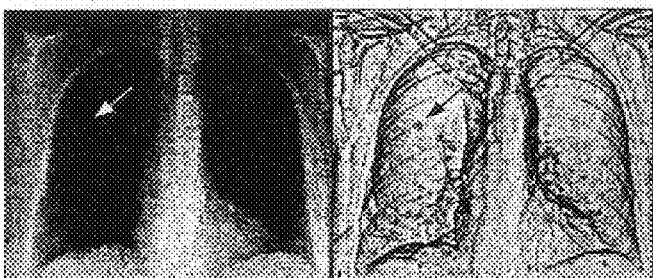
FIG. 7a. FIG. 7b.
FIG. 7c. FIG. 7d.
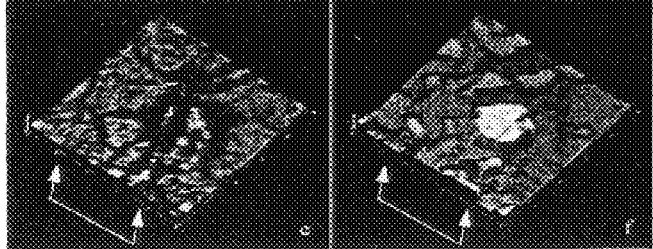
FIG. 7e. FIG. 7f.
FIG. 7.

FIG. 8a. FIG. 8b. FIG. 8c.
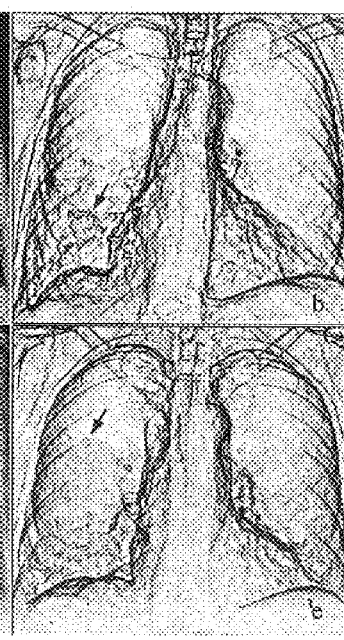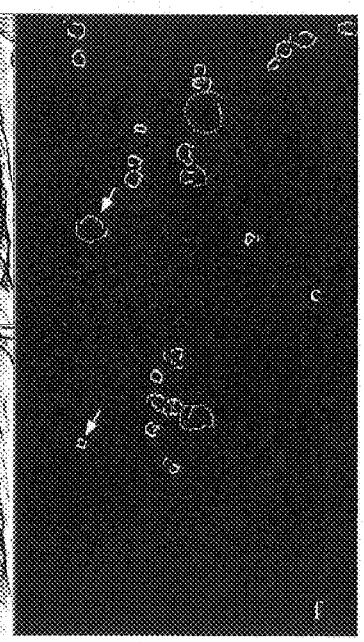
FIG. 8. FIG. 8d. FIG. 8e. FIG. 8f.

COMPUTER-ASSISTED METHOD AND APPARATUS FOR THE DETECTION OF LUNG NODULES

CROSS-REFERENCE TO RELATED APPLICATION

This application claims priority from provisional application "Computer-Assisted Method and Apparatus for the Detection of Lung Nodules," Ser. No. 60/029,335, filed on Oct. 30, 1996.

BACKGROUND OF THE INVENTION

1. Field of the Invention

The invention relates to the development of computer-assisted diagnostic (CAD) methods for the analysis of digital x-ray images or gray-scale images generated by other digital sensors. More particularly, the invention relates to the use of CAD methods for the analysis of chest x-rays for the detection of lung nodules.

2. Description of Related Art

The use of computer-assisted diagnostic (CAD) methods has been proposed as a second opinion strategy for various medical imaging applications that include breast screening using digital mammography and lung nodule detection. The goals of the CAD methods are to improve sensitivity by increasing the detection of potentially significant suspicious areas and to improve specificity by reducing false-positive interpretations.

Lung nodule detection using conventional planar chest x-ray film typically does not exceed a detection rate of 70%. Typically x-ray CT is used as a follow-up diagnostic procedure. Although x-ray CT has a greater sensitivity of detection, the detection and classification of all LNs within the 3 D volume (stacked 2 D slices) poses a significant logistical and time-consuming research problem (Giger et al., 1994; Buckley et al., 1995). CAD methods are therefore important for both x-ray chest imaging and x-ray CT. However, until now, CAD methods have been found to result in a high rate of false positives (J. S. Lin et al., 1995). The problems associated with CAD methods for lung nodule detection can be attributed to several factors, including that:

1. Lung nodules typically have small structures having very low image contrast and that are spatially distributed in a nonuniform tissue background and image noise;
2. Lung nodules are often adjacent to or hidden by camouflaging structures such as the rib cage, media sternum, or blood vessels, the ribs and vessels being oriented so that they may be viewed in both lateral and cross-section configuration; and
3. Lung nodule features such as circularity, irregularity, and compactness are often similar to blood vessels viewed end on.

Various CAD lung nodule detection schemes have been realized with two successive steps:

1. Segmentation of suspicious areas; and
2. Differentiation of nodules from lung and chest structures (S. B. Lo et al., 1995).

The former can be considered region-of-interest (ROI) localization of suspicious areas, and the latter as a typical pattern recognition problem. Several algorithms proposed in the literature, such as thresholding, 2 D profile matching, and morphological operations, use intensity characteristics on a 2 D matrix and are sensitive to overlapping lung structures, which often appear as stronger signals than nodules in the image (S. B. Lo et al., 1993; M. L. Giger et al., 1990 b). Two-dimensional linear filtering also suffers from high computation cost and a lack of multiscale analysis. A general schematic diagram for the current method of detecting lung nodules is presented in FIG. 1.

Previous methods incorporating CAD modules (Lin et al., 1996; Giger et al., 1994) have limitations that degrade the sensitivity and specificity of LN detection, including:

1. CAD modules that are not automatic (operator dependent) and use fixed parameters that are often image dependent as opposed to methods that adapt, for example, to the image noise;
2. Single-scale filtering methods are used for image enhancement or segmentation that do not optimally differentiate LNs from other clinical features with similar pixel intensity characteristics and do not preserve image details, as opposed to multiresolution or multiorientation wavelet transform methods; and
3. Feature extraction is not optimally performed in all domains (grey level, morphological, texture).

Previously disclosed image-enhancement methods have included:

1. Unsharp-masking techniques and gradient generation for edge detection using the Sobel or Roberts operator (Tahoces et al., 1991; Daponte et al., 1988);
2. 2 D surface fitting to correct for nonuniform background (Katsuragawa et al., 1988);
3. Morphological operations to selectively enhance circularity of the LNs (Giger et al., 1990 a); and
4. Generalized unsharp-mashing techniques by generating difference images of an enhanced image (2 D profile matching or Fourier transform methods) and a smoothed image (linear or median filters) (Giger et al., 1990 b; Lo et al., 1993).

Image segmentation methods include global thresholding, adaptive or local thresholding techniques based on pixel intensity histograms and trained classifiers to identify lung fields or asymmetry in chest images (Duryea et al., 1995; McNitt-Gray et al., 1994; Armato et al., 1994).

Feature extraction has proved to be a very difficult task in order to differentiate LNs from end-on vessels or recognize LNs located near rib cage crossings. Methods include region growing to generate various grey-level and morphological features (Matsumoto et al., 1992; Wu et al., 1994). Classification methods used have included discriminant analysis, rule-based schemes, and trained neural networks (Wu et al., 1994; Lo et al., 1993, 1995; Lin et al., 1996). These classification methods aim at reducing the false positive rate in the suspicious area segmentation, the sensitivity of which has been on the order of 70% with a large false positives (FPs) to image ranging from 4 to 12. It is reported that these methods can reduce the false positive rate. Because of the differences and limitation of the databases used, it is difficult to evaluate and compare quantitatively these CAD methods.

Wavelet theory has recently been developed as a unifying framework. Multiresolution signal processing, which is used in computer vision, subband coding developed for image/speech compression, and wavelet series expansion as developed in applied mathematics, has recently been recognized as a different aspect of signal processing theory (Rioul et al., 1991). The application of wavelet theory in mammogram processing includes feature enhancement (Laine et al., 1995), detection of microcalcifications (Qian et al., 1995 b), differentiation of mass from normal tissue (Karssemeijer, 1994). For example, Laine et al. (1995) used linear, exponential, and weighted functions successfully for the modification of the coefficients of dyadic wavelet transform for improving the local feature visibility. This work is focused on image enhancement for improved visual diagnosis, as opposed to improving feature extraction.

SUMMARY OF THE INVENTION

It is therefore an object of the present invention to provide a method, system, and apparatus for improved sensitivity and specificity in lung nodule detection in digital x-ray imaging to enable early and accurate diagnosis.

It is another object to provide such a method, system, and apparatus for improved localization of suspicious areas.

It is a further object to provide such a method, system, and apparatus that permits improved differentiation between lung nodules and overlapping objects such as ribs and end-on vessels.

It is an additional object to provide such a method, system, and apparatus for use as a "second opinion" strategy.

It is yet another object to provide such a method, system, and apparatus for use in remote diagnoses.

It is yet a further object to provide a preprocessed image useful for detecting a lung nodule.

It is yet an additional object to provide a data file containing a preprocessed image useful for detecting a lung nodule.

These and other objects are achieved by the present invention, which is specifically directed towards x-ray chest imaging. A further use is for x-ray computed tomography (CT) imaging. Broadly, the method and apparatus utilize a theory and application of a multiresolution wavelet transform and a multiorientation wavelet transform, iteratively applied to enhance and segment normal tissue structures and suspicious lung nodules for improved feature extraction. Such feature extraction is believed to improve the sensitivity of detection and reduce a false positive detection rate for lung nodules.

The modular CAD method and apparatus in a preferred embodiment comprise (see Glossary of terms in Table 1):

1. Image noise suppression using a multistage nonlinear tree-structured filter (TSF) using fixed parameters and/ or an adaptive multistage nonlinear filter (AMNF);
2. Selective image enhancement or segmentation of clinical features using, for example, multiresolution (M-channel) tree-structured wavelet transforms (TSWTs), which permit improved differentiation of normal anatomical structures from suspicious lung nodule (LN) areas;
3. Multiorientation (N) directional wavelet transforms (DWTs) for additional directional feature enhancement or extraction of specific structures such as the rib cage or blood vessels;
4. A 1.5-dimensional (1.5 D) filter for additional enhancement and segmentation of suspicious lung nodule areas; and
5. Neural networks (NNs) or fuzzy binary decision trees (FBDTs) for classification using features computed in the pixel intensity, morphological, directional texture, and connectivity domains.

TABLE 1

Glossary of terms and abbreviations for the CAD modules proposed for enhancement, segmentation, and classification in lung nodule detection

| Applications | |
|---|---|
| Enhancement: | Increasing the visibility of the medically important information for interpretation by a human or a machine |
| Segmentation: | Specifically extracting suspicious areas using image processing techniques |
| Classification: | Pattern recognition techniques to differentiate LN areas from normal structures |
| Enhancement Modules | |
| TSF: | Tree-structured filter for image noise suppression with fixed parameters |
| AMNF: | Adaptive multistage nonlinear filter for image noise suppression |
| TSWT: | Tree-structured wavelet transform for selective image enhancement |
| DWT: | Directional wavelet transform for multiorientation feature enhancement |
| 1.5DF: | 1.5-dimensional filter for LN enhancement |
| Segmentation Modules | |
| AC: | Adaptive clustering for suspicious area extraction |
| 1.5D: | 1.5-dimensional filter for LN segmentation |
| Classification Modules | |
| FBDT: | Fuzzy binary decision tree for recognition of suspicious areas |
| MFNN: | Mixed-feature neural network for recognition of suspicious areas |
| Operators and Filter Parameters | |
| LO: | Linear operator for AMNF |
| OS: | Order statistic operator for AMNF |
| M: | Number of channels for TSWT |
| N: | Number of directions for DWT |
| Clinical Evaluation | |
| FROC: | Free response operator characteristics |
| TP: | True positive detection rate |
| FP: | False positive detection response |

The CAD modules and methods have been designed and optimized to permit:

1. Fully operator-independent operation to reduce inter-observer variation;
2. The preservation of image details for each CAD module using the unique properties of the wavelet transforms; and
3. Improved feature extraction in the grey level, morphological (shape), directional texture, and connectivity domains.

The invention can be used as a "second opinion" strategy or "prereader strategy" at either a centralized location or a remote location using teleradiology/telemedicine techniques.

Although not meant to be limiting, the method, system, and apparatus of the present invention are applicable to images such as nodules present in a digital chest x-ray image. It is believed that the combined approach of visual interpretation of enhanced images and computer aids should thus reduce the inter- and intraobserver variation in image interpretation at, for example, centralized or remote locations and/or when using networked medical computer workstations.

The invention, in terms of computer software design, relates to the use of image processing CAD modules that allow features to be extracted more effectively.

Typically the apparatus includes a medical image workstation using high-resolution monitors to display raw, enhanced, and segmented images to permit better visual interpretation.

Among the important aspects of this method, system, and apparatus are the use of multiresolution/multiorientation wavelet transforms in the image preprocessing for improved feature extraction and the use of higher-order transforms (M,N) for improved performance or application for different sensors.

An additional important feature is the development and use of a 1.5 D circular pattern filter and a spatial and multiscale analysis to resolve the problem presented by overlapped objects and to detect objects of different sizes.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 7 illustrates representative results for segmentation of a proven lung nodule partially overlapped by the rib structure. (a) The raw image prior to filtering; (b) an enhanced image of anatomical and nodule structures; (c) enhanced rib structure image; (d) a decomposed image showing directional features; (e) 3 D plot of a subregion of the raw image containing a known nodule; and (f) the nodule enhanced and with the rib structure subtracted out, preparatory to segmentation.

FIG. 8 Two representative cases illustrating the segmentation of suspicious lung nodule areas. Depicted are: (a,d) raw images; (b,e) enhanced images using AMNF/TSWT; (c,f) segmented suspicious lung nodule areas.

DETAILED DESCRIPTION OF THE PREFERRED EMBODIMENTS

A description of the preferred embodiments of the present invention will now be presented with reference to FIGS. 1–15.

The system comprises, and the method comprises the use of, a plurality of CAD modules, preferably those listed in Table 1, applied to a raw digital x-ray image for the determination and localization of a suspicious nodule in the lung. The broadest embodiment is presented in the logic block diagram of FIG. 1, wherein a raw image in digitized or direct digital form (Box 90) is subjected to image noise suppression and enhancement using image processing techniques (Box 15). Next image segmentation is applied, also using image processing techniques (Box 20). Finally, suspicious areas are classified using pattern recognition techniques (Box 30). In a preferred embodiment, the resulting enhanced images comprise a plurality of enhanced images having experienced a plurality of processing steps. The enhanced images are then displayed with the raw image (Box 35), a visual comparison permitting an improved interpretation of a detected nodule. Similarly, images containing the detected nodule and false positives are shown The images can also be stored or transmitted electronically to another site by any of the methods known in the art (Box 35).

Figure 1:
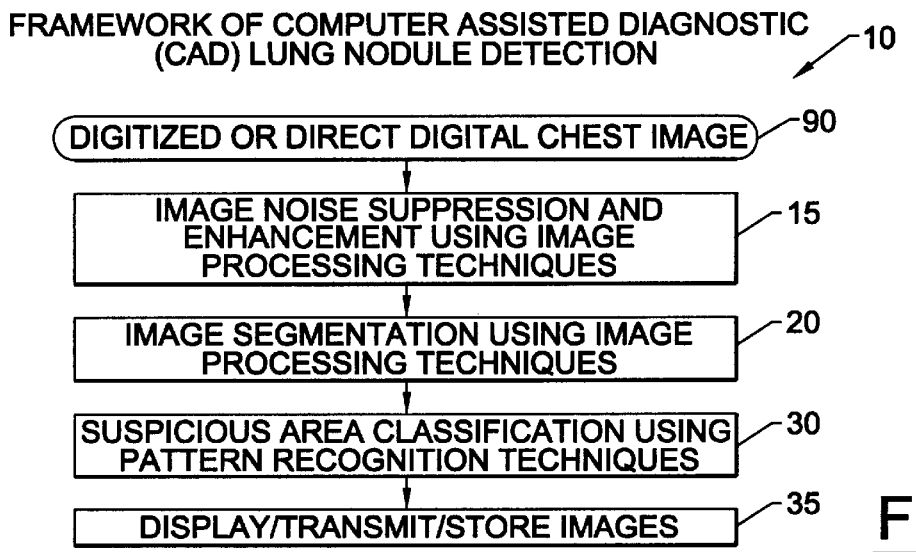
FIG. 1 is a block diagram of the computer-assisted diagnosis (CAD) method of the present invention for lung nodule detection. In this embodiment planar x-ray chest images generated by digitized film or direct x-ray detection may be used.
Figure 2:
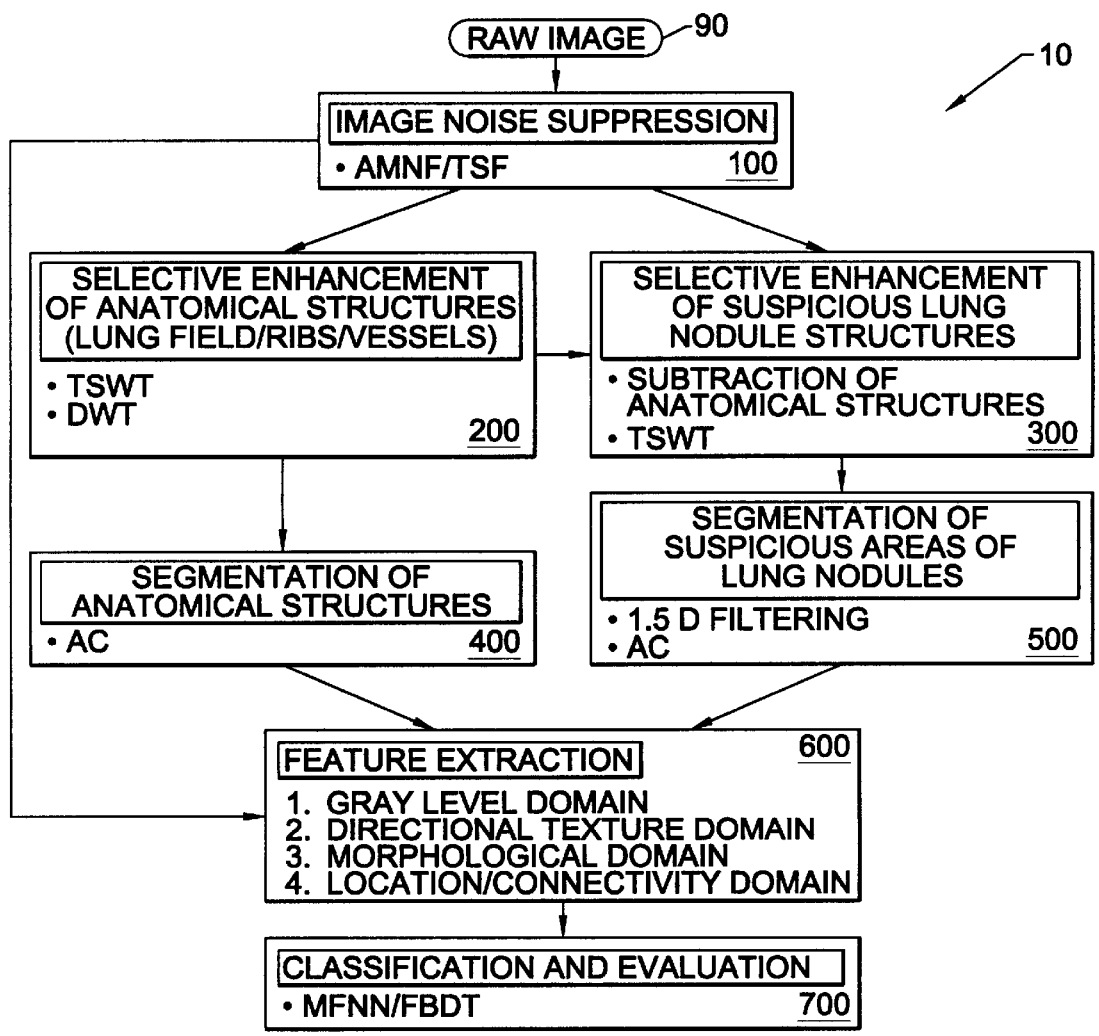
FIG. 2 is a detailed block diagram showing the use of image processing CAD modules for lung nodule detection using digitized chest x-ray images.

An overview logic diagram for a preferred embodiment of the invention 10 appears in FIG. 2, which illustrates the interconnections of the CAD modules utilized. The image preprocessing modules and methods (Boxes 100–500) provide the ability to extract features from four domains: the grey-level (Box 100), the directional texture (Box 200), the morphological (Box 500), and the location and connectivity (Boxes 400,500) domains.

Image Noise Suppression

The digital x-ray image is preferably first filtered (FIG. 2, Box 100) by either a multistage tree-structured nonlinear filter (TSF) with fixed parameters or an adaptive multistage nonlinear filter (AMNF) to suppress image noise while preserving image details potentially to improve feature extraction in the gray-level domain or as a preprocessing filter for application of multiresolution and multiorientation wavelet transforms. Digital images generated by either x-ray film digitizers or by direct digital x-ray sensors currently under development generate various sources of noise in the detection process, as described previously (Qian et al., 1994 a,b).

The presence of noise or structured noise may degrade the ability to extract features in the gray-level domain or texture features with high directional sensitivity using the DWT CAD module. Two noise-suppression filters are applied, although these are not meant to be limiting: (a) a tree-structured nonlinear filter (TSF) with fixed parameters for a given digital sensor that is computationally efficient; and (b) an adaptive multistage nonlinear filter (AMNF), which is more suitable for universal application to different sensors with varying noise characteristics and for image enhancement. Both filters are applied on a pixel-by-pixel basis throughout the full image. Both filters are preferably incorporated into the modular CAD structure shown in FIGS. 1 and 2.

Tree-Structured Filter (TSF). The multistage tree-structured filter (TSF) used in the present invention (Block 100, FIG. 2) comprises a three-stage filter designed with central weighted median filters (CWMFs) as subfiltering blocks (Bauer and Qian, 1991; and FIG. 1, Qian et al., 1994 a) applied to each pixel within the filter window (see FIG. 2, Qian et al., 1994 a). The purpose of the TSF is to suppress noise while preserving image features before an application of multiresolution/multiorientation wavelet transforms for image enhancement and segmentation (FIG. 2), which may be sensitive to image noise. This filter assists in reducing false postive detection rate of LNs. Modified windows of the filter bank in the first stage and comparison of the filtered image to the raw image for each stage are used to preserve image detail of anatomical tissue structures, with significantly improved noise reduction compared with conventional single-stage filters such as the median filter. Details of the theoretical basis for this TSF and analysis of its performance have been published using both simulated images with varying noise content and representative images (Qian et al., 1994 a, the discussion of which is hereby incorporated herein by reference).

Adaptive Multistage Nonlinear Filter (AMNF). The AMNF comprises a two-stage filter that incorporates an adaptive operation. The first stage contains, by way of example, five different conventional filters with varying filter window sizes, namely, a linear filter (9×9 window), α trimmed mean (7×7 window), α trimmed mean (5×5 window), α trimmed mean (3×3 window), and median filter (3×2 window) [Qian et al., 1995 b, FIG. 2, Eq. (6–15)]. The second stage uses a signal-dependent weighting factor, based on the local signal activity, and its variance is used to select the appropriate filter in the first stage. For example, in the uniform-background regions of the image with slowly changing signal intensity, a smoothing filter with a large window may be chosen to suppress noise. Alternatively, in regions of varying signal intensity of important clinical tissue structures or suspicious areas (lung nodules), a filter with a small window may be chosen better to preserve image details during noise suppression.

The first stage of the filter may also include other filters, such as the previously described TSF further to preserve image details of suspicious areas and adaptively selected, as previously described.

This AMNF filter design has been described in Qian et al. (1995 a,b), the contents of which are incorporated herein by reference.

The filtered image comprises an image in the gray-level domain. This filtered image is used for image enhancement and segmentation of normal anatomical structures and suspicious lung nodule areas (FIG. 2, Boxes 200, 300, 400, 500).

An AMNF can be used both for image noise suppression and image enhancement (Box 100). The AMNF can be cascaded with a hybrid TSWT as an additional selective image enhancement step (Qian et al., 1995 b). The AMNF is an extension of the previously discussed TSF. The AMNF has proved suitable for both additive and multiplicative signal-dependent noise. The AMNF adaptively selects different filters, either a linear operator (LO) or order statistic operator (OS), on a pixel-by-pixel basis (Qian et al., 1995 b, FIG. 2).

Image Enhancement

Multiresolution Tree-Structured Wavelet Transform (TSWT). The AMNF is cascaded with an M-channel tree-structured wavelet transform (TSWT) for image-selective enhancement of normal anatomical features (FIG. 2, Box 200), such as the lung field (FIG. 3, Box 220), rib structure (Box 230), or blood vessels (Box 240). These normal anatomical features are subtracted from the filtered image (FIG. 4, Box 310), this step comprising a linear weighted subtraction where the weighting coefficient for each case is determined empirically using the training image database. The M-channel TSWT decompostion is used to decompose the subtracted image with selective reconstruction of the $M^2$ subimages to enhance the suspicious lung nodule areas (FIG. 4, Box 320). The branch to Box 500 is for segmentation of the enhanced suspicious nodule areas.

Figure 3:
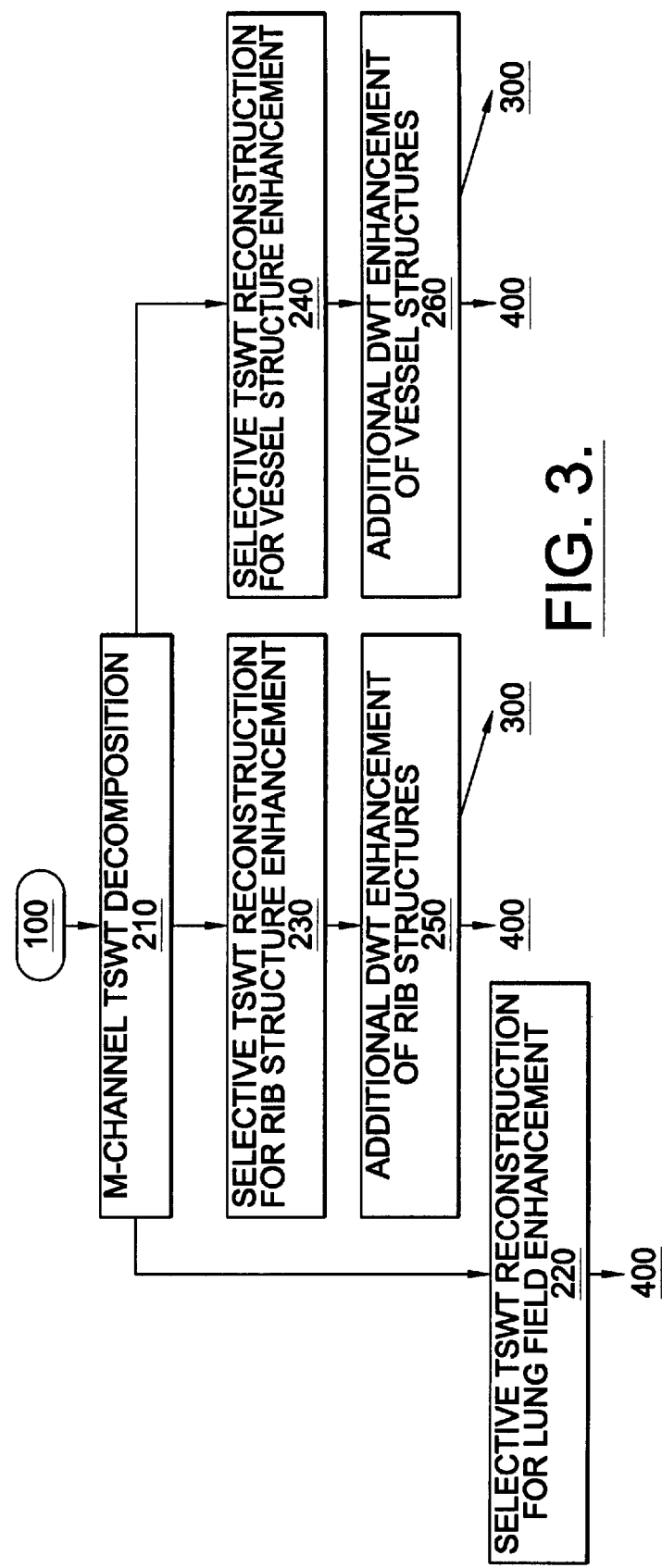
FIG. 3 is a block diagram illustrating details of block 200 of FIG. 2 for selective enhancement of anatomical structures.
Figure 4:
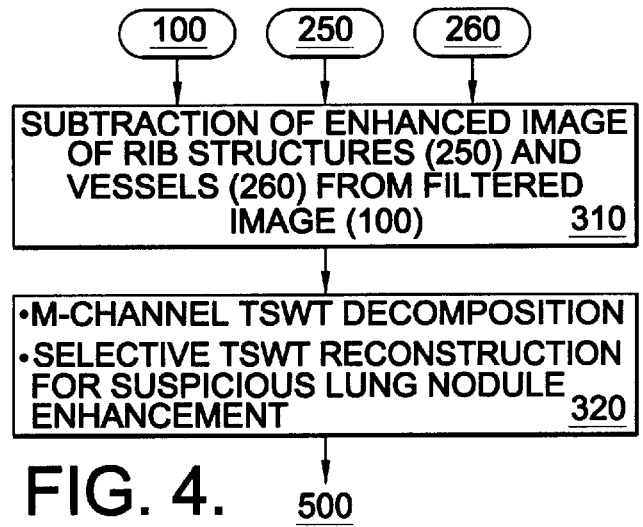
FIG. 4 is a block diagram illustrating details of block 300 of FIG. 2 for selective enhancement of suspicious lung nodule structures.
Figure 5:
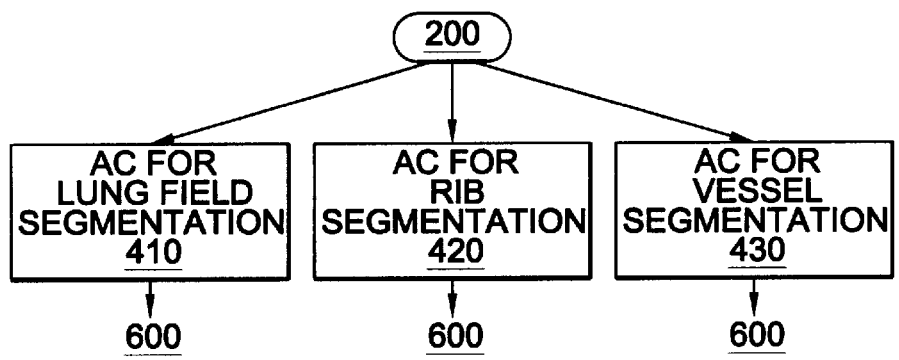
FIG. 5 is a block diagram illustrating details of block 400 of FIG. 2 for segmentation of anatomical structures.

For the M-channel TSWT the multiresolution wavelet transform originally proposed by Mallat (1989 b) is used as a basis for selective image enhancement (FIG. 3, Box 210). The Debauches 16-wavelet transform is used, wherein image decomposition into subimages using an M-channel TSWT is implemented on a quadrature mirror filter bank (QMF), as an exemplary method (Qian et al., 1993; 1995 a). M-channel wavelet transforms implemented on QMFs preserve the properties of near-perfect reconstruction and allow for higher-order M transforms ($M^2$ subimages) to allow for more selective image enhancement (Boxes 200,300). The selective enhancement of normal anatomic structures and suspicious lung areas is achieved by selecting subimages using visual criteria and a training image database with both normal chest images and representative images containing known lung nodules.

Image segmentation is an image decomposition in which the image is decomposed into spatially separated components (Jain, 1989). The pixels in each component have certain similarity in their features, e.g., gray level. Two major techniques for image segmentation are the boundary-based approach and the region-based approach. In the boundary-based approach, boundary information is determined based on edge detection. The main idea in region-based segmentation is to identify various regions in an image that have similar features.

For chest images, the boundary of a lung nodule is frequently difficult to determine by edge detection because of the low contrast of the images and ill-defined edges. In contrast, the region-based segmentation method is more suitable for segmentation because the pixels within a suspicious area will generally have more uniform intensity and are often brighter than the surrounding tissue. However, the suspicious lung nodule areas are imbedded in a nonuniform background signal due to surrounding tissue such as the rib structure and may be hidden behind this rib structure. To develop an automatic segmentation method for application to the full chest image, some form of selective image enhancement of the suspicious areas relative to the background is required prior to multiresolution segmentation.

Qian et al. have previously used an M=2 channel tree-structured wavelet transform (TSWT) for selective image enhancement of microcalcification clusters in digital mammography, preceded by an adaptive multistage nonlinear filter (AMNF) (Qian et al., 1995 b). The theoretical basis for the M-channel TSWT (M=2, 4, 8, . . . ) and implementation on different filter banks including QMFs has been described (Qian et al., 1994 b, 1995 a,b). Herein the M-channel TSWT is utilized for selective enhancement of suspicious areas, implemented on QMFs (Qian et al., 1994 b). This technique is also described in U.S. Pat. No. 5,576,548, the disclosure of which is incorporated herein by reference.

Selective reconstruction of the $M^2$ subimages is proposed for selective image enhancement of normal tissue structures and suspicious areas. Higher-order M channels are used to provide improved image enhancement relative to the background signal, as may be required for the varying gray-scale characteristics of different digital sensors, that is, by more selective reconstruction of the higher-order $M^2$ subimages. Such selective reconstruction of the subimages is currently obtained by visual criteria and the use of a training data set with known ground truth normal chest images and known lung nodule cases. The selection of subimages for reconstruction is currently basen on visual criteria using a training image database.

For higher-order M channels (M=4), visual selection may prove to be a time-consuming task. We believe that an adaptive selection of subimages may be possible by a selection of appropriate features in each subimage such as the use of related correlation and energy function criteria within subimages (Qian et al., 1995 b).

Directional Wavelet Transform (DWT). The next enhancement module, the DWT, is a wavelet transform for multiresolution signal decomposition originally developed for digital mammography but discovered to be useful for the present application as well. The DWT method, initially explored for mammographic mass detection, is a modification based on the Mallat et al. (1989 b) wavelet representation for multiresolution signal decomposition. A key concept for DWT is to choose a set of wavelet functions that have a high orientation selectivity. The input image is decomposed by the DWT to yield directional features as illustrated in FIG. 7d. The order N of the directionality of the DWT may be selected (N=8, 16, 32, . . . ), where the higher-order N is used for enhancement or extraction of fine image details such as blood vessels. The N-DWT is therefore applied to the enhanced images of the rib structure and blood vessel structure, for example (FIG. 3, Boxes 230,240), using the same training image database, to further enhance directional features associated with these structures (Boxes 250, 260). The order N of the multiorientation transform (DWT) is selected for cases using the same training database, where typically N=8 is used, but higher-order N>8 is possible to enhance the finer structure of the blood vessels. The branches to Boxes 300 and 400 are shown where further image preprocessing is performed to differentiate lung nodules from the above anatomical structures.

Mallat (1989 a) discussed the relationship between multichannel frequency decomposition and the application of wavelet models. This work includes the conceptual basis for a multiorientation wavelet transform (MWT) but does not provide the wavelet function.

Grossman and Morlet (1984) have proposed a wavelet function that can be modified to generate the multiorientation wavelet transform conceptually suggested by Mallat (1989 a), with an appropriate choice of parameters. However, this MWT is only an approximate solution for the proposed application because of limited directional sensitivity. To demonstrate this point, we describe the basis and results for the MWT based on Mallat (1989 a) and Grossman and Morlet (1984), the wavelet function used being commonly referred to as the Morlet wavelet function. To obtain the desired directionality of the wavelet transform, we have implemented a modification to the Morlet wavelet function, referred to as the directional wavelet transform (DWT). The DWT has varying orders of directions (N=8, 16, . . . ), where a higher order of N may be used to match the resolution required for feature extraction, such as fine-detail structures like blood vessels.

The DWT has been designed to allow the directional features in the image to be enhanced for improved segmentation of normal tissue structures and suspicious lung nodule areas.

The modification to the Morlet DWT to extract directional features is first theoretically developed to clarify the novelty in the modified DWT of the present invention.

General Wavelet Transform and Directional Wavelet Transform. Let $\psi(x,y) \in L^2(\mathbb{R}^2)$ be a function whose Fourier transform $\Psi(w_x, w_y)$ satisfies $$\int_{-\infty}^{+\infty} \frac{|\psi(sw_x, sw_y)|^2}{s} ds = C_\psi < +\infty, \forall (w_x, w_y) \in \mathbb{R}^2 \qquad (1)$$

The wavelet transform of a function $f(x,y) \in L^2(\mathbb{R}^2)$ at scale s and a point (u,v) is defined by $$Wf(s, (u, v)) = \int_{-\infty}^{+\infty} \int_{-\infty}^{+\infty} f(x, y) s\psi(s(x-u), s(y-u)) dx dy \qquad (2)$$

Let $$\psi_s(x,y) = s\psi(sx, sy) \qquad (3)$$

$$\bar{\psi}_s(x,y) = \psi_s(-x,-y) \qquad (4)$$

Then the wavelet transform of f(x,y) can be rewritten as a convolution product $$Wf(s,(u,v)) = f * \bar{\Psi}_s(u,v) \qquad (5)$$

If the wavelet function $\psi^i(x,y)$ has orientation (direction) selectivity, then the wavelet transform within orientation i is called a directional wavelet transform, and is defined by $$Wf^i((u,v),s) = \iint f(x,y) s\psi^i(s(x-u), s(y-u)) dx\, dy \qquad (6)$$

Its Fourier transform is $$WF^i(s, \omega_x, \omega_y) = F(\omega_x, \omega_y) \Psi^i(\omega_x/s, \omega_y/s) \qquad (7)$$

where $F(\omega_x, \omega_y)$ and $\Psi^i(\omega_x, \omega_y)$ are the Fourier transforms of f(s,y) and $\psi^i(x,y)$, respectively.

Assume the angle of the highest sensitivity of the wavelet function is $\theta_i$; then the MWT within orientation i can be formulated in the Fourier domain with polar coordinate as follows:

$$WF(s, \rho, \theta, \theta_i) = F(\rho, \theta)\Psi(\rho/s, \theta, \theta_i) \qquad (8)$$

where $$\rho = (\omega_x^2 + \omega_y^2)^{1/2} \qquad (9)$$

$$\theta = \arctan(\omega_y/\omega_x) \qquad (10)$$

From the standpoint of filtering, the operation above can be considered to be a multiresolution directional filtering.

Figure 10:
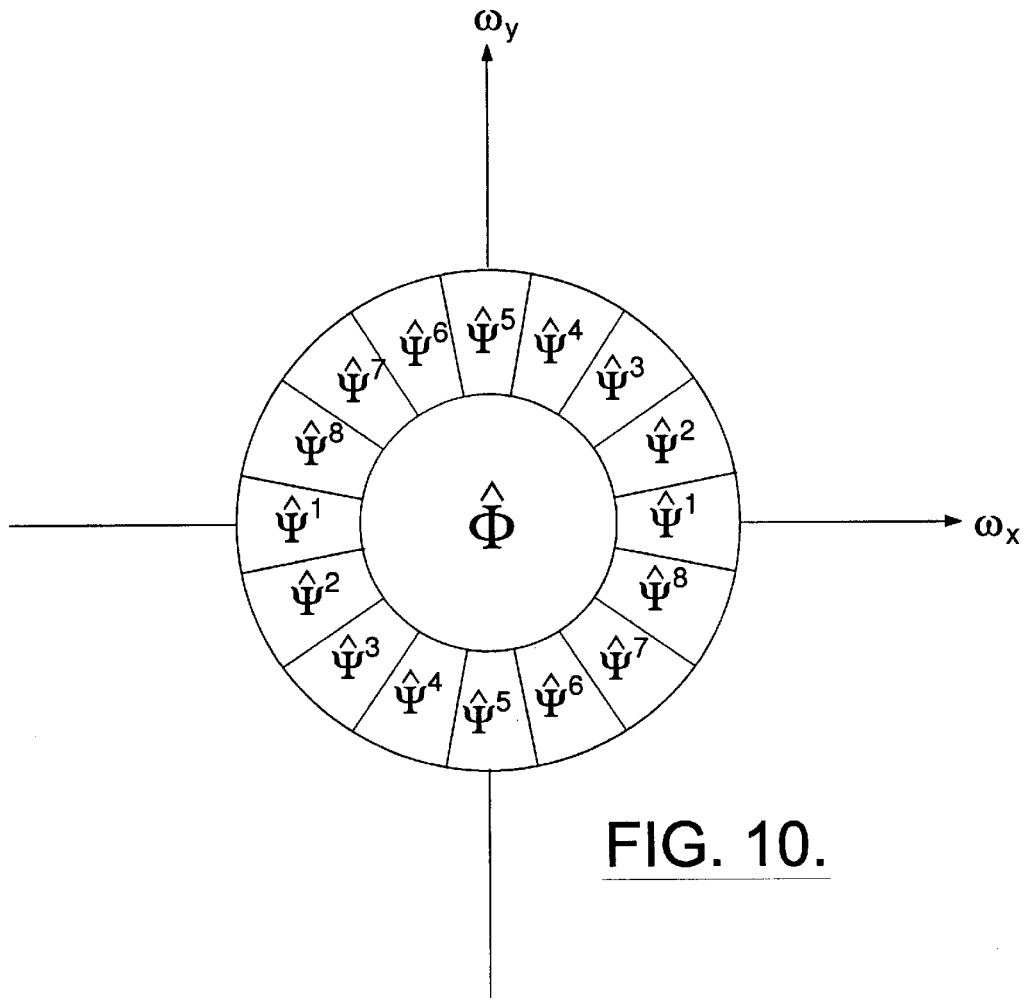
FIG. 10 is a diagram of multiorientation wavelet transform (MWT) decomposition in the Fourier domain of support of $\Psi(\omega_x,\omega_y)$ into 8 wavelets $\Psi^i(\omega_x,\omega_y)$, $1 \leq i \leq 8$, having different orientation selectivities, wherein the supports of the functions $\Psi^i(\omega_x,\omega_y)$ are symmetrical about 0 and are rotated from one another.

Referring to FIG. 10, the decomposition in the Fourier domain of support into 8 wavelets $\Psi^i(\omega_x, \omega_y)$, $1 \leq i \leq 8$, having different orientation selectivities is shown.

Figure 11:
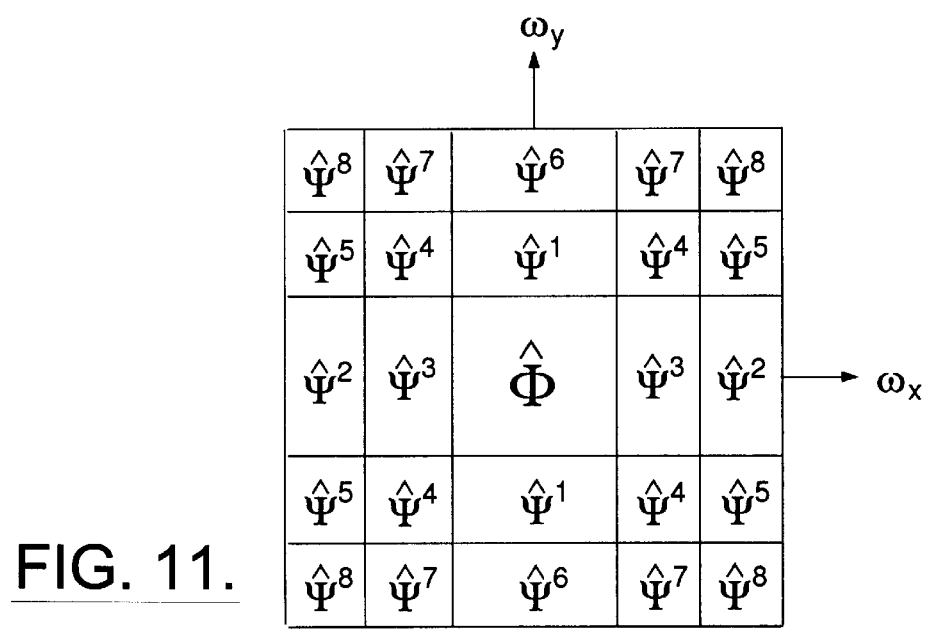
FIG. 11 is a diagram of a multiresolution wavelet decomposition to illustrate that the conventional wavelet transform does not have a directional constraint.

Referring to FIG. 11, a comparison is made to the multiresolution wavelet transform that does not have directional constraints such as the MWT or DWT.

Theoretical Basis for MWT Using the Morlet Wavelet Function. If $\alpha$ and/or $\beta$ is sufficiently large, the following Gabor function can be an approximation of the well-known Morlet wavelet function (Unser et al., 1990).

$$\Psi^i(x, y) = g(x', y') \exp[j(\alpha x' + \beta y')] \qquad (11)$$

$$g(x', y') = \frac{1}{\lambda(2\pi)^{1/2}\sigma^2} \exp - \frac{(x/\lambda)^2 + (y')^2}{2\sigma^2} \qquad (12)$$

where $$x' = x \cos \theta_1 + y \sin \theta_1 \qquad (13)$$

$$y' = x \sin \theta_1 + y \sin \theta_1 \qquad (14)$$

Its Fourier transform is $$\Psi(\omega_x, \omega_y) = \exp - \frac{\lambda^2(\omega'_x - \alpha)^2 + (\omega'_y - \beta)^2}{\sigma^2} \qquad (15)$$

where $\omega_x', \omega_y'$ are the rotations of $\omega_x$ and $\omega_y$.

Figure 12:
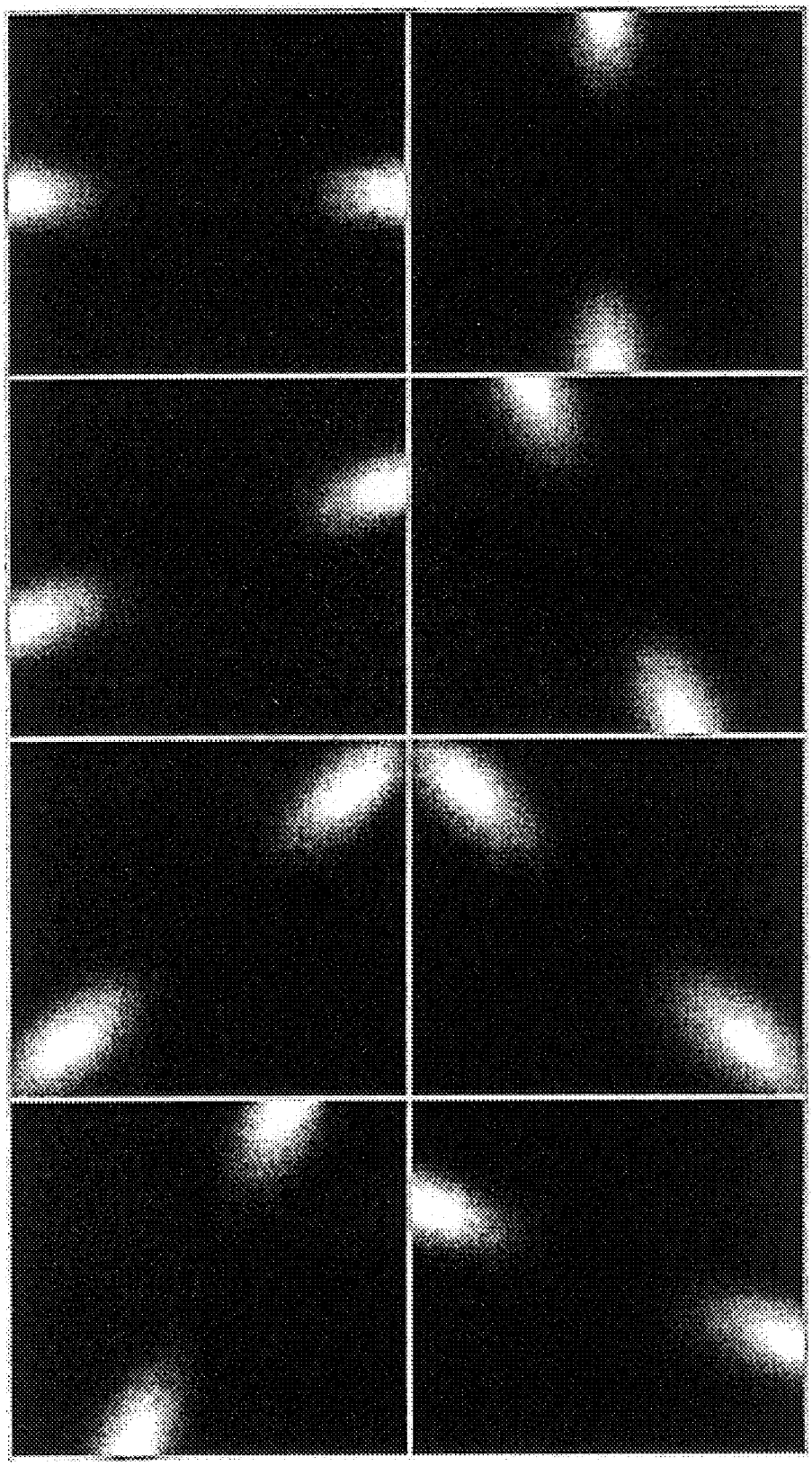
FIG. 12 is a diagram of an MWT decomposition in the Fourier domain of support $\Psi(\omega_x,\omega_y)$ into N=8 wavelets $\Psi^i(\omega_x,\omega_y)$, $1 \leq i \leq 8$, by using the Morlet wavelet function with different parameters, showing limitation in directionality.

With no loss of generality, set $\beta = 0$. If $\alpha$ is large enough and the parameters ($\sigma$ and $\lambda$) are selected properly, then we can obtain different directional images at different resolution by applying the above directional wavelet function with different $\theta_i$. Referring to FIG. 12, images of eight directional Morlet wavelet functions in the Fourier domain tuned to orientations $i\pi/8$, $0 \leq i \leq 7$, respectively, are shown, where the higher signal intensity reflects the bandwidth range and the directionality of the transform.

The limitations of the directionality for the MWT is indicated in FIG. 12, where the bandwidths for each direction are not well defined. To improve the directional selectivity, a modification to the Morlet wavelet function is used to obtain the directional wavelet function, which is described mathematically as follows:

$$\Psi(\omega_x, \omega_y) = 1 - \exp - \frac{\omega_x'^2 + \omega_y'^2}{\sigma_1^2} \exp - \frac{\omega_y'^2}{\omega_y'^2} \frac{\ln \sigma_2}{\tanh^2 \alpha} \qquad (16)$$

where $\omega_x', \omega_y'$ are the rotation coordinates of $\omega_x$ and $\omega_y$, $$\omega_x' = \omega_x \cos \theta + \omega_y \sin \theta \qquad (17)$$

$$\omega_y' = \omega_x \sin \theta + \omega_y \cos \theta \qquad (18)$$

$\theta$ is the direction of the wavelet function; the parameters $\alpha$ and $\sigma_2$ are related to the bandwidth of the orientation; $\sigma_1$ is the lower cutoff frequency of the directional wavelet function. For the general case of an N-directional wavelet transform, the angle $\theta = i\pi/N$, where N may be equal to 4, 8, 16, . . . , for example.

It is believed that the use of the N-directional wavelet transform for directional image enhancement can be matched to the resolution of the digitized image with the use of higher-order (N=8, 16, . . . ) wavelet transforms. Similarly, the use of the N-directional wavelet transform for feature extraction can be matched to the resolution of the image or to extract higher-resolution features by using higher-order (N=8, 16, . . . ) wavelet transforms (FIG. 3, Boxes 250,260).

Figure 13:
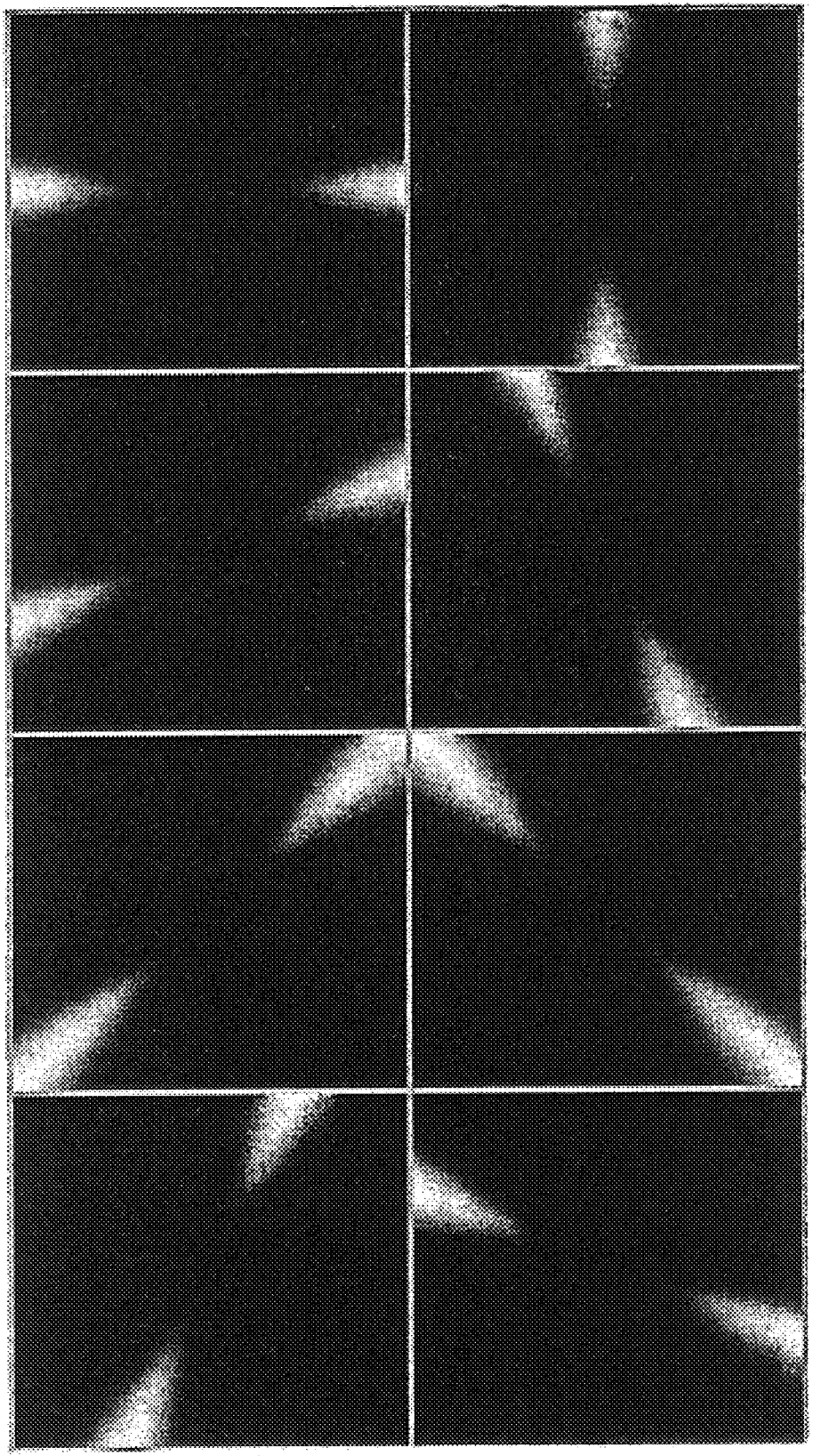
FIG. 13 is a photograph of images of the N=8 directional wavelet transform (DWT) in the Fourier domain with orientations $(i-1)\pi/8$, $1 \leq i \leq 8$, showing the improvement in directionality of the wavelet transform.
Figure 14:
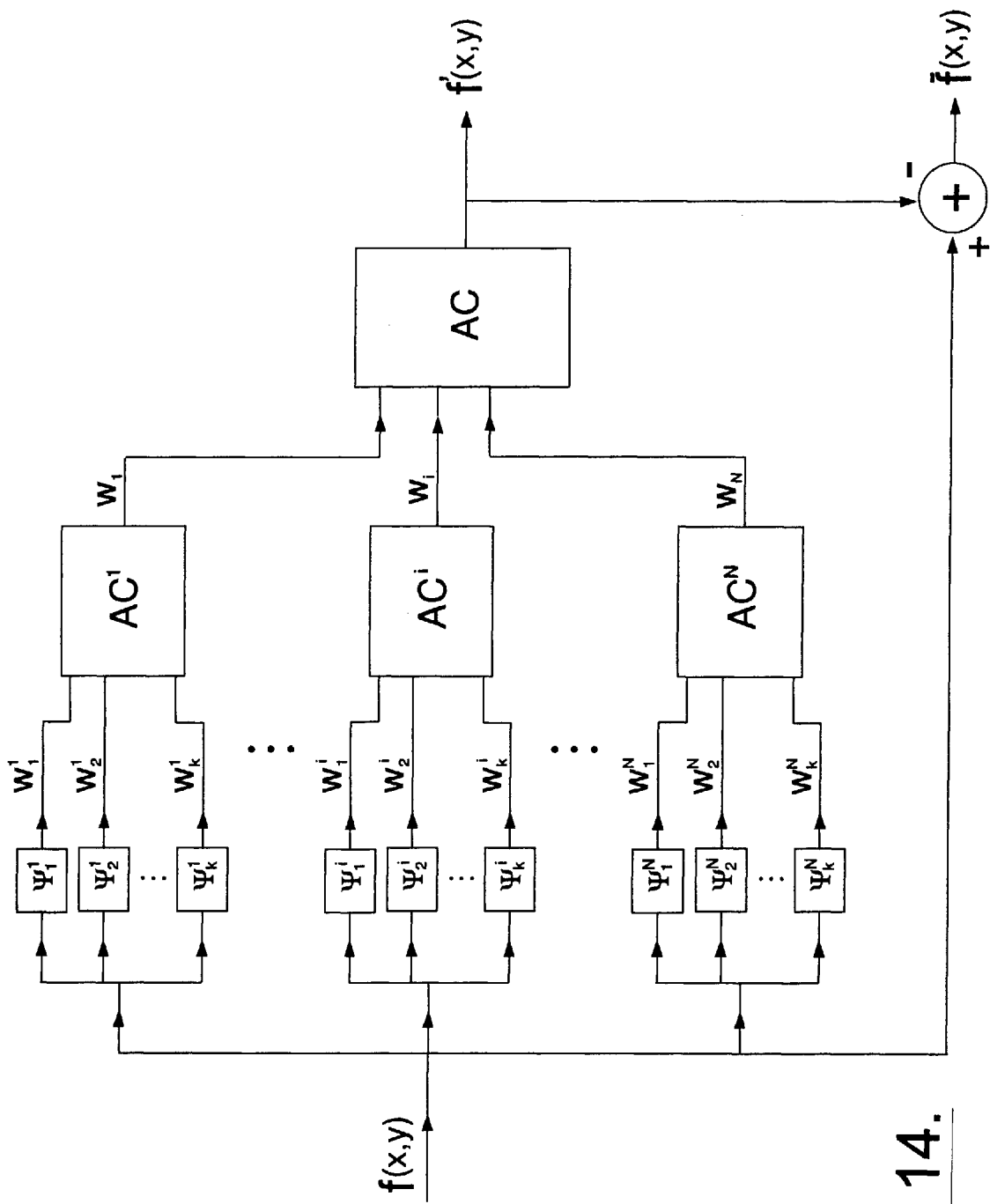
FIG. 14 is a block diagram showing image feature decomposition, using the DWT and an adaptive combiner.

Referring to FIG. 13, a set of spectral images of eight wavelet functions with different directions ($i\pi/8$), $0 \leq i \leq 7$ (i.e., N=8), are shown for the proposed DWT, where the narrower bandwidth and improved directionality can be seen compared with the Morlet DWT.

Referring to FIG. 7, for the chest image f(i,j), two output images are obtained from the feature decomposition by directional wavelet analysis, namely, a directional feature image to allow feature extraction (FIG. 7d), a directional-feature-enhanced image created by adding directional features to the noise-suppressed image (FIG. 7c).

The directional texture image (FIG. 7b) is expressed as $$f'(x, y) = \sum_{i=1}^{N} W_i \sum_{j=1}^{K} W_j^i \Psi_j^i(f(x, y)) \qquad (19)$$

where $\Psi^i(*)$ refers to the output of a wavelet transform at direction i and resolution j; $W_i$ and $W_j^i$ are the weights for standard adaptive combiners (see FIG. 14).

The enhanced-image version of the original noise-suppressed image is expressed as (FIG. 7c):

$$\tilde{f}(x, y) = f(x, y) + \alpha f'(x, y) \qquad (20)$$

These input images are used for both additional enhancement steps, segmentation, and feature extraction, as shown in FIGS. 2–6.

Image Segmentation and Additional Enhancement

Figure 6:
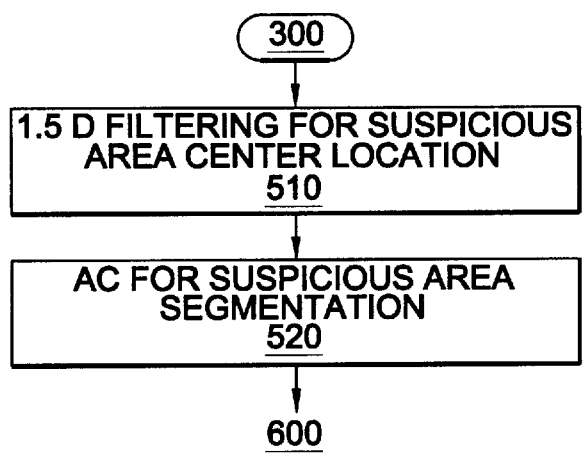
FIG. 6 is a block diagram illustrating details of block 500 of FIG. 2 for segmentation of suspicious lung nodule structures.

The 1.5-Dimensional Circular Pattern Filter. In order to accomplish the objective of increasing the sensitivity and specificity of the detection of lung nodules, an appropriate filter has been designed for additional enhancement and segmentation of suspicious LNs, as shown in FIG. 6, Box 510. This filter is used to locate the center and approximate size of each suspicious nodule area, so that the following process, adaptive clustering (Box 520) can achieve boundary segmentation in chest images, where the image background is highly nonuniform. Such a filter should have sensitivity to circular patterns or area circularity, which is an important feature of lung nodules in x-ray images. The filter should also not be sensitive to overlapping objects such as ribs. The filter of the present invention has a dimension of 1.5.

Multiscale filters are used on the image, and a stability analysis performed in order to localize lung nodules of different sizes.

The design of the 1.5 D circular pattern filter is based on the following exemplary criteria:

1. It should be sensitive to a circular pattern;
2. It should be insensitive to overlapping structures; and
3. It should provide a normalized output to provide adaptability for different image resolutions and multiscale analysis.

To achieve these criteria, only the boundary characteristics of a circular area are considered. The concept is that the gradient directions along a circular boundary, presuming that the area is brighter than the background, should be oriented to the center of the area. This gradient feature will remain correct on the majority of the boundary even when the nodule is overlapped by another structure. This is where 2 D profile matching fails.

Starting from the input image $I_0(x,y)$, we calculate two normalized gradient direction images, $I_x(x,y)$ and $I_y(x,y)$, as follows:

$$G_r = \sum_{n=-w/2}^{x/2} I(x+n, y) \times h_n$$

and $n = -2, -1, 0, 1, 2.$ $h_n = 1$ if $n < 0$ $h_n = -1$ if $n > 0$ $h_n = 0$ if $n = 0$ $$I_x(x, y) = G_r(s, y) \bigg/ \sqrt{G_r(x, y)^2 + G_c(x, y)^2}$$

$$G_c(x, y) = \sum_{n=-w/2}^{w/2} I(x, y+n) \times h_n$$

$$I_y(x, y) = G_c(x, y) \bigg/ \sqrt{G_r(x, y)^2 + G_c(x, y)^2}$$

The filter is represented by a list of vectors, also normalized, as $(F_{x,k}(x_i,y_i), F_{y,k}(x_i, y_i))$, where $(x_i,y_i)$ represents the positional disparity from the point to be filtered and k is a scale factor. $(x_i,y_i)$ is a sample point on a circular curve. Coupled circular-pattern-sensitive filters are imposed:

$F_{y,k}(x,y) = \sin(\theta(k,x,y))$ $F_{x,k}(x,y) = \cos(\theta(k,x,y))$

A measurement of the existence of a circular pattern for a given point (x, y) is calculated as follows:

$$P_c(x, y) = \frac{1}{N} \sum_{i=1}^{N} (F_{x,k}(x_i, y_i) I_x(x+x_i, y+y_i) + F_{y,k}(x_i, y_i) I_y(x+x_i, y+y_i))$$

where k is a scale factor.

Since the measurement $P_c(x,y)$ is a normalized output, a thresholding or an adaptive selection of objects can be performed.

The next step in the method comprises spatial and multiscale analysis of the filtered result obtained by the 1.5 D filter. This analysis locates suspicious areas in both the spatial and scale domains.

The analysis in the spatial domain comprises an extraction of local extremities related to different scales. Only one extremity is assumed to exist in a limited area in the spatial domain.

The analysis in scale space has two purposes:

1. Using stability estimation to reduce false positives; and
2. Obtaining a more precise estimation of the area boundary location and the size of the area.

This analysis is concerned with extremity extraction in scale space and the fact that a real circular area should appear stable across several scales, which is usually used in multiscale signal analysis. Here it is assumed that only one extremum exists in scale space relating to a given image area.

Figure 9:
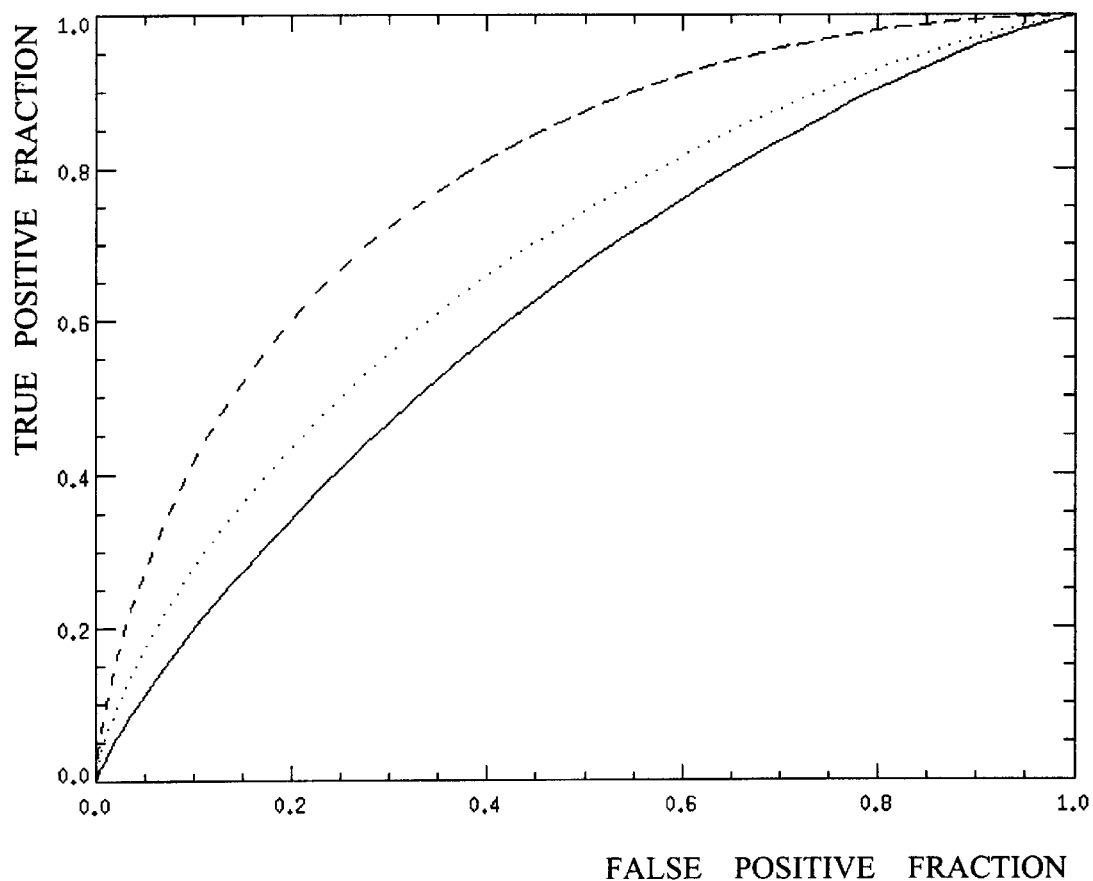
FIG. 9 Representative receiver operator characteristic (ROC) results showing the advantages of the 1.5 D filter. The results are shown for (a) the 1.5 D filter applied to raw image data (- - -); (b) matched filtering on edge-enhanced preprocessed image (•••); and (c) matched filtering on a raw image (—).

In comparison with a generalized Hough transform scheme, no edge detection is needed, which makes the current invention suitable for subtle pattern detection and provides a lower computation cost. The method is target oriented, and is suitable for exploiting contextual information. Further, multiscale analysis is an important step for detecting multiscale nodules and reducing false positives. In FIG. 9 representative receiver operator characteristics (ROC) results illustrate the advantages of the 1.5 D filter. Data were analyzed from regions of interest where a circular and square pattern were simulated and randomly distributed within a digitized image of the chest. The higher ROC curve reflects the better performance of the 1.5 D filter (curve a).

Following the application of the 1.5 D filter (Box 510), adaptive clustering as above is performed for suspicious area segmentation (Box 520) to segment out the boundary of the suspicious nodule. This information is used for feature extraction to reduce the false positive detection of nodules in the steps outlined below.

Adaptive Clustering. Adaptive clustering is a generalization of methods known in the art, such as the K-means method. Modifications have been made for the preferred embodiment to adapt to changes in the statistical properties from each image analyzed. This is an iterative approach beginning with an initial segmentation of the enhanced image (Qian et al., 1997), and parameters are adaptive to allow a selective segmentation of enhanced anatomical structures (FIG. 5, Boxes 410,420,430) and suspicious lung nodule areas (FIG. 6, Boxes 510,520).

With the input from the 1.5 D filter (Box 510), the adaptive clustering module is directed to segment only circular regions, performing the technique in regions of interest with adaptive sizes based upon the guidance of the 1.5 D results.

AC in the present embodiment is made to adapt to changes in characteristics from pixel to pixel in the same image and changes in statistical properties from image to image. The clustering criteria of the AC algorithm consist of two elements: the distance (measured by mean-square error) of the pixel intensity to the cluster centroid and the neighbor constraint, which is based on the Gibbs density distribution. Because the clustering centroid is calculated based on a sliding window instead of the whole image, such as that in the K-means algorithm, it can be made adaptive to local characteristics. Also, because a different constraint coefficient is taken based on the standard variance of the image, it is made adaptive to different images: segmentation of lung field (Box 410, FIG. 5), ribs (Box 420), and vessels (Box 430).

With the iteration of the algorithm, the segmentation obtained by adaptive clustering is statistically an approximation of the maximum posterior estimation (Pappas et al., 1992).

Feature Extraction

The feature extraction of the present invention is based on the enhancement and segmentation (FIG. 2, Box 600) and includes, by way of example only:

1. A region, extracted from the raw or enhanced image, that contains the suspicious area defined by the segmentation process;
2. Grey-level feature calculation, such as the mean gradient of the area boundary, mean grey-level difference, and grey-level variation;
3. Morphological feature calculation, such as area size, compactness, and multiscale shape descriptors;

4. Directional feature calculation, such as template (linear, circular, and starlike) matching using multiscale directional texture; and
5. Positional and connectivity measurement calculation, such as distance to linear structures, position in the lung field, and certain specific anatomical knowledge in parametric form.

Classification and Evaluation

By way of example only, a classifier can be used to reduce the false positive detection of lung nodules. For example, this could include, as shown in Table 1, a fuzzy binary decision tree (FBDT) or a mixed-feature neural network (MFNN) (Box 700). The use of a particular classifier is not intended to be a limitation on the present invention, but is cited to illustrate the importance of image preprocessing for improved feature extraction.

Apparatus and Resultant Images

CAD Algorithm Design. The key software technology involves the use of the following for improved feature extraction for LN detection:
1. Nonlinear filters for image noise suppression;
2. Multiresolution and multidirectional wavelet transforms for image enhancement;
3. 1.5-dimensional filtering and multiscale enhancement for LN localization; and
4. Adaptive clustering for segmentation of normal anatomical structures and lung nodules.

The code in the present embodiment is generated in the C language, although this is not intended as a limitation, and includes an extensive library of wavelet bases for both image analysis and compression.

Figure 15:
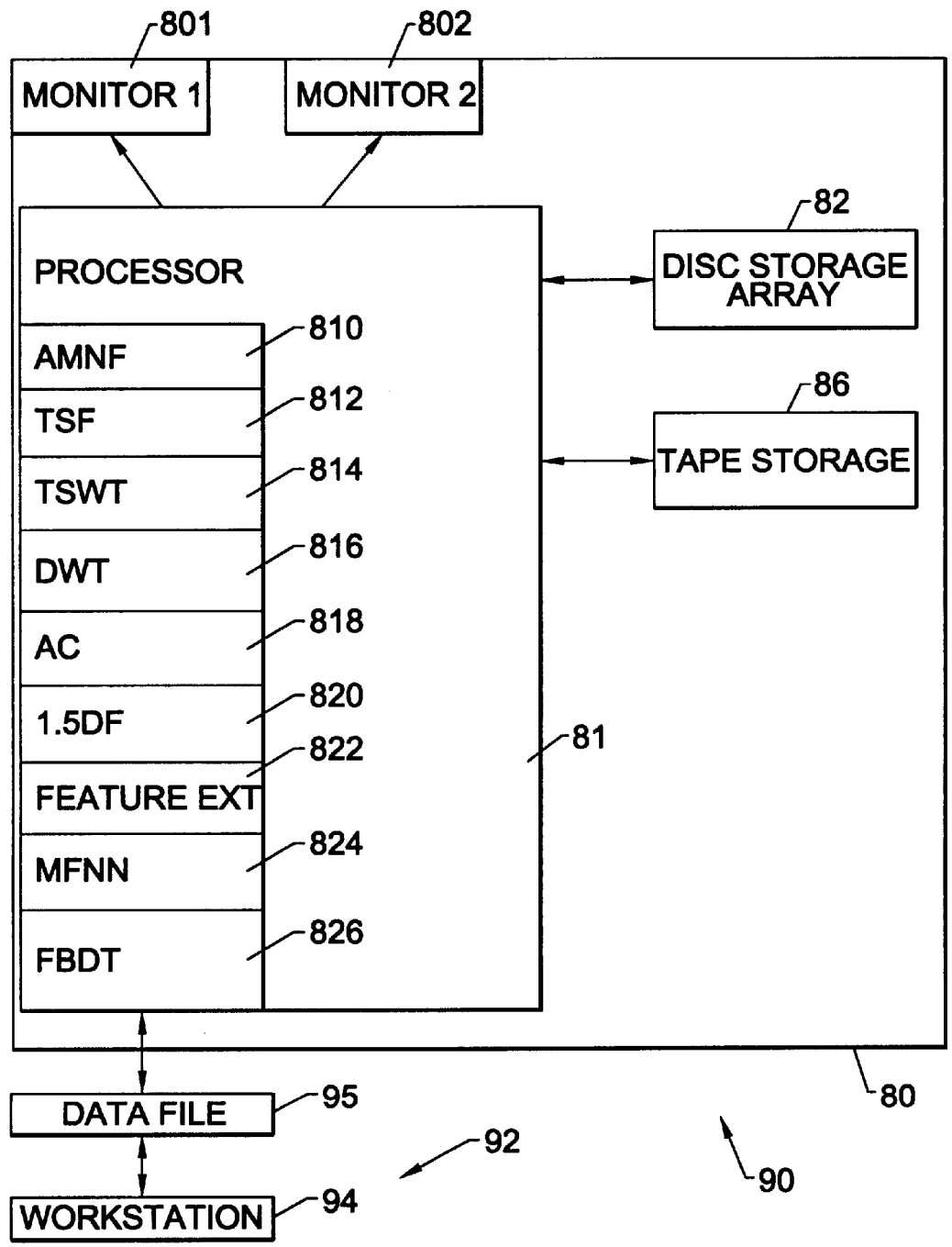
FIG. 15 is a schematic diagram of the apparatus of the present invention, indicating both local and remote image processing capabilities.

Medical Workstation. The proposed medical workstation 80, in an exemplary embodiment, includes a processor 81 in communication with two high-resolution, high-luminance computer monitors 801,802 suitable for gray-scale interpretation of digital x-ray images, as shown in FIG. 15. The processor 81, which in the present embodiment comprises a SUN-SPARC 4 Workstation, is also in communication with fast disc storage arrays 82 and the necessary hardware to display images of the order of 5 Mbytes or better, as required for digital images. Processor 81 is further in communication with a tape backup unit 86.

The processor 81 has resident therein the CAD modules of the present invention: AMNF 810, TSF 812, TSWT 814, DWT 816, AC 818, 1.5 DF 820, feature extraction module 822, MFNN 824, and FBDT 826.

The proposed method and apparatus would employ software for fully operator-independent review of the images; that is, each CAD module requires no operator input for the analysis of images by a physician.

It is believed that the operator-independent nature of the image review process will reduce the inter- and intraoperator variability in detecting and localizing lung nodules at either a central reading location 90 or any remote location 92 where the same or a compatible workstation 94 is available. Thus an image generated at a first location 92 can be sent in digital form to a processing location 90, where the CAD preprocessing and processing modules of the present invention 10 could be applied to generate images such as shown in FIGS. 7 and 8. A data file 95 is then transferrable back to the remote location 92, and a series of images displayed there. Thus the present invention should be construed to include all images and data files containing such images that are generated by the system and method disclosed herein.

Similarly, it is believed that the image enhancement, coupled with segmentation and detection of the nodules, at least partly compensates for the performance of the monitor and may allow low-end monitors to be used for remote diagnosis as required for referring physicians. It is also believed that segmentation of the suspicious areas, as opposed to prompts on the original image, reduces the disturbing or distracting effect of the presence of false positives, which may be visually rejected based on their location and segmented shape.

Images for Nodule Detection. Representative results for the segmentation of a proven nodule that is partially overlapped by the rib structure using a digitized chest x-ray film. The images are shown in FIG. 7, wherein: FIG. 7a is the raw image prior to filtering (Box 100); FIG. 7b the enhanced image of all anatomical structures including nodules using the AMNF/TSWT (Boxes 100,200); FIG. 7c an enhanced image for rib structures using the DWT (Box 200); FIG. 7d the direct decomposed image showing directional features (Box 200); FIG. 7e a 3 D plot of the subregion of the raw image containing the nodule; and FIG. 7f the enhanced nodule with subtraction of the rib structure (Box 300) that can be used for subsequent segmentation by both a 1.5 D filter and AC.

In FIG. 8 two representative cases illustrate: FIGS. 8a and 8d, the raw image; FIGS. 8b and 8e, an enhanced image by AMNF/TSWT; and FIGS. 8c and 8f, the segmented suspicious lung nodule areas. Features indicated in FIG. 2 are then used to reduce the false positive detection rate.

Significance anti Future Directions

Diagnostic radiology has been undergoing a decade-long transition from x-ray screen/film sensors to direct or real-time x-ray detection systems, with the intent of replacing film reading using light box technology by high-resolution computer monitors. Key problems that need to be addressed for filmless diagnostic x-ray imaging include:
1. Physician resistance to reading from computer monitors because of their low luminance and grey-scale contrast compared to film/light box reading;
2. Potential variability in reading using image enhancement methods that are not automatic such as grey-scale windowing/thresholding; and
3. The absence of fully automatic CAD methods that may reduce the variability in reading by different observers.

These factors also limit the potential for teleradiology reading for difficult diagnostic procedures that require good resolution and image contrast. The present invention addresses these issues for the difficult clinical model involving LN detection by x-ray chest imaging. The modular CAD disclosed may be readily modified in an alternate embodiment for different x-ray sensors with varying resolution and grey-scale characteristics as required for teleradiology/telemedicine applications.

Thus it is believed that the method of the present invention, which comprises nonlinear filtering using boundary information and 1.5 D filtering, should result in higher sensitivity and specificity than previously reported CAD methods. It is also believed that the multiscale analysis of the present invention is critical to improving the sensitivity and specificity in lung nodule detection.

References

Armato et al., *Med. Phys.* 21, 1761–68, 1994
Bauer and W. Qian, *Proc. IEEE Pacific Rim Conf. on Communications, Computers and Signal Proc.* 2, 494–97, 1991)

Buckley et al., *Radiology* 196, 395–400, 1995
Daponte et al., *IEEE Trans. Med. Imag.* 7, 1988
Duryea et al., *Med. Phys.* 22, 183–91, 1995
Giger, M. L., et al., *Radiographics* 10, 41–51, 1990 a
Giger, M. L., et al., *Med. Phys.* 17, 861–65, 1990 b
Giger, M. L., et al., *Investigative Radiology* 29, 459–65, 1994
Grossmann, A., and J. Morlet, *SIAM J. Math.* 15, 723–36, 1984
Jain, A. K., *Fundamentals of Digital Image Processing.* Prentice Hall, Englewood Cliffs, 1989.
Karssemeijer, N., "Recognition of stellate lesions in digital mammograms," *Digital Mammography,* A. G. Gale et al., eds., Elsevier Science B.V., 1994.
Katsuragawa, S., et al., *Med. Phys.* 15, 311–19, 1988
Laine, A., et al., *IEEE Engrg. Med. Biol.* 14, 536–50, 1995
Lin, J. S., et al., *J. Digital Imag.* 8, 132–41, 1995
Lin, J. S. et al., *IEEE Trans. Med. Imag.* 15, 206–17, 1996
Lo, S. B., et al., *J. Digital Imag.* 6, 48–54, 1993
Lo, S. B., et al., *IEEE Trans. Med. Imag.* 14, 711–18, 1995
Mallat, S., "Multifrequency channel decompositions of images and wavelet models," *IEEE Trans. of Acoustic, Speech, and Signal Processing* 37(12), 1989 a.
Mallat, S., "A theory for multiresolution signal decomposition: The wavelet representation," *IEEE Trans. on Pattern Analysis and Machine Intelligence* 11(7), July, 1989 b.
Matsumoto, T., et al., *Investigative Radiol.,* Aug., 587–97, 1992.
McNitt-Gray, M. F., et al., *Proc. SPIE, Image Processing* 2167, 1994.
Pappas, T. N., "An adaptive clustering algorithm for image segmentation," *IEEE Trans. on Signal Processing* 40(2), April 1992.
Qian, W., L. P. Clarke, et al., "Tree-structured nonlinear filter and wavelet transform for microcalcification segmentation in mammography," *Proc. of the IS&T/SPIE Annual Symposium on Electronic Imaging, Science & Technology, San Jose, Calif.,* 1993.
Qian, W., L. P. Clarke, M. Kallergi, and R. A. Clark, "Tree-structured nonlinear filters in digital mammography," *IEEE Trans. on Medical Imaging* 13(1), Mar. 1994 a.
Qian, W., L. P. Clarke, et al., "Digital mammography: m-Channel quadrature mirror filters for microcalcification extraction," *Computerized Imaging and Graphics* 18(5), 301–14, Sept./Oct., 1994 b.
Qian, W., L. P. Clarke, M. Kallergi, B. Zheng, and R. A. Clark, "Wavelet transform for computer assisted diagnosis (CAD) for digital mammography," *IEEE Engineering in Medicine and Biology Magazine, Invited Paper,* 14(5), 561–69, 1995 b.
Qian, W., M. Kallergi, L. P. Clarke, H. D. Li, R. A. Clark, and M. L. Silbiger, "Tree-structured nonlinear filter and wavelet transform for microcalcification segmentation in digital mammography," *Med. Phys.* 22(8), 1247–54, 1995 a.
Qian et al., *Academic Radiology,* 1997, in press
Rioul, O., and M. Vetterli, *IEEE Signal Proc. Mag.* 8(4), 1991.
Tahoces et al., *IEEE Trans. MI* 10, 330–35, 1991
Unser, M., and M. Eden, "Multiresolution feature extraction and selection for texture segmentation," *IEEE Trans. on Pattern Analysis and Machine Intelligence* 11(7), July 1990.
Wu et al., *J. Digital Imag.* 7, 196–207, 1994

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not intended to be limited to the exact details of construction or practice.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A computer-assisted method for detecting a lung nodule comprising the steps of:

suppressing noise in a digital chest image;

enhancing and segmenting anatomical structures in the noise-suppressed image;

enhancing a potentially suspicious area in the noise-suppressed image; and further enhancing and segmenting the potentially suspicious area with the use of a filter having sensitivity to a shape feature of a lung nodule and having relative insensitivity to an overlapping object.

2. The method recited in claim 1, wherein the suspicious area further enhancing and segmenting step comprises applying a 1.5-dimensional filter having sensitivity to a circular pattern.

3. The method recited in claim 1, wherein the suspicious area segmenting step further comprises performing adaptive clustering to segment out a boundary of the suspicious area.

4. The lung-nodule detection method recited in claim 1, wherein the noise-suppressing step comprises adaptively filtering noise.

5. The lung-nodule detection method recited in claim 4, wherein the adaptive noise-filtering step comprises applying an adaptive nonlinear multistage nonlinear filter.

6. The lung-nodule detection method recited in claim 5, wherein the adaptive nonlinear multistage nonlinear filter is adapted to adaptively select a filter on a pixel-by-pixel basis.

7. The lung-nodule detection method recited in claim 6, wherein the filter-selecting step comprises selecting among a plurality of filters comprising a linear operator and an order statistic operator.

8. The lung-nodule detection method recited in claim 1, wherein the anatomical structure enhancing step comprises applying a wavelet transform to the noise-suppressed image.

9. The lung-nodule detection method recited in claim 8, wherein the wavelet transform applying step comprises applying one or more of a tree-structured wavelet transform and a directional wavelet transform.

10. The lung-nodule detection method recited in claim 1, wherein the anatomical structure enhancing step comprises applying a wavelet transform to the enhanced image.

11. The lung-nodule detection method recited in claim 10, wherein the wavelet transform applying step comprises applying a tree-structured wavelet transform and the anatomical structures segmenting step comprises applying adaptive clustering.

12. The lung-nodule detection method recited in claim 1, wherein the suspicious area enhancing step comprises subtracting enhanced anatomical structures from the noise-suppressed image.

13. The lung-nodule detection method recited in claim 12, wherein the suspicious area enhancing step further comprises applying a wavelet transform to the noise-suppressed image.

14. The lung-nodule detection method recited in claim 13, wherein the wavelet transform applying step comprises applying a wavelet-based multiresolution/multiorientation transform comprising a bank of wavelet filters implemented on two-stage adaptive combiners.

15. The lung-nodule detection method recited in claim 1, further comprising the steps, following the enhancing and segmenting steps, of:
performing feature extraction on the segmented anatomical structures and potentially suspicious areas;
differentiating a suspicious area from the potentially suspicious areas based upon the feature-extraction step; and
classifying the suspicious area as a true positive or a false positive.

16. The lung-nodule detection method recited in claim 15, wherein the feature extraction step comprises extracting a region containing a potentially suspicious area and performing a feature calculation in a grey-level domain, a direction texture domain, a morphological domain, and a connectivity domain.

17. The lung-nodule detection method recited in claim 15, wherein the feature extraction step further comprises calculating positional and connectivity measurements.

18. The lung-nodule detection method recited in claim 17, wherein the suspicious area selecting and classifying steps comprise applying a neural network to the extracted region.

19. The lung-nodule detection method recited in claim 17, wherein the neural network applying step comprises applying a mixed-feature neural network using backpropagation with Kalman filtering.

20. A system for detecting a lung nodule contained in a digital chest image comprising:
means for suppressing noise in a digital chest image;
means for enhancing and segmenting anatomical structures in the noise-suppressed image;
means for enhancing potentially suspicious areas in the noise-suppressed image; and
filter means for segmenting the potentially suspicious area, the filter means having sensitivity to a shape feature of a lung nodule and having relative insensitivity to an overlapping object.

21. The system recited in claim 20, further comprising:
means for performing feature extraction on the raw and segmented anatomical structures and potentially suspicious areas;
means for classifying a suspicious area as a true positive or a false positive from the potentially suspicious areas based upon input of computed features from the feature-extraction step.

22. A system for detecting a lung nodule contained in a digital chest image comprising:
a filter for suppressing noise in a digital chest image;
a wavelet transform adapted to enhance anatomical structures in the noise-suppressed image;
a subtraction algorithm for removing the enhanced anatomical structures from the noise-suppressed image;
a wavelet transform adapted to enhance a potentially suspicious areas in the noise-suppressed image; and
a 1.5-dimensional circular pattern filter for additionally enhancing a suspicious area from the enhanced, anatomic-structure-subtracted image.

23. The system recited in claim 22, further comprising:
means for performing a feature extraction in a grey-level domain, a direction texture domain, and a morphological domain, for performing feature extraction on the segmented anatomical structures and potentially suspicious areas; and
a neural network for classifying the suspicious area.

24. A system for detecting a lung nodule contained in a digital chest image comprising:
means for accessing digital chest image data;
a processor in electronic communication with the data accessing means, the processor having resident therein a plurality of computer-assisted diagnostic modules for processing the digital chest image data comprising:
a filter for suppressing noise in a digital chest image;
a wavelet transform adapted to enhance anatomical structures in the noise-suppressed image;
a wavelet transform adapted to enhance a potentially suspicious area in the noise-suppressed image; and
a circular pattern filter for selectively further enhancing the suspicious area.

25. The system recited in claim 24, wherein the modules further comprise software means for performing a feature calculation in a grey-level domain, a direction texture domain, a morphological domain, and a location/connectivity domain, for performing feature extraction on the enhanced and segmented anatomical structures and potentially suspicious area; and
a neural network for classifying the suspicious area as a potential lung nodule or a false positive based upon input of computed features from the feature-extraction module.

26. A modular software system for processing digital chest image data to detect a lung nodule, the system comprising:
a filter module for suppressing noise in digital chest image data;
a wavelet transform module adapted to enhance anatomical structures in the noise-suppressed image;
a wavelet transform module adapted to enhance a potentially suspicious areas in the noise-suppressed image; and
a 1.5-dimensional circular pattern filter module for further enhancing the enhanced suspicious area.

27. The system recited in claim 26, further comprising:
a feature calculation module for performing feature extraction on the raw image and the segmented anatomical structures and potentially suspicious areas in a grey-level domain, a direction texture domain, a morphological domain, and a connectivity domain; and
a neural network module for selecting a suspicious area from the potentially suspicious areas based upon the feature-extraction step and for classifying the suspicious area.

28. A data file containing a selected and classified suspicious area in a chest image, the data file having been created with the use of the software system of claim 26.

29. A method for performing image processing to detect a lung nodule in a digital chest image at a first site, the image having been collected at a second site remote from the first site:

electronically transmitting the image from the second site to the first site;

preprocessing the image to segment out a potentially suspicious area by:

suppressing noise in the image;

enhancing and segmenting anatomical structures in the noise-suppressed image;

enhancing a potentially suspicious area in the noise-suppressed image; and further enhancing the potentially suspicious area with the use of a filter having sensitivity to a shape feature of a lung nodule and having relative insensitivity to an overlapping object;

segmenting the further enhanced potentially suspicious area with the use of adaptive clustering; and electronically transmitting the processed image from the first site to the second site.

30. A method for performing image processing to determine for a presence of a lung nodule in a digital chest image at a first site, the image having been collected at a second site remote from the first site:

electronically transmitting the image from the second site to the first site;

processing the image to determine whether a potentially suspicious area is present by segmenting out a potentially suspicious area by:

suppressing noise in the image;

enhancing and segmenting anatomical structures in the noise-suppressed image;

determining whether a potentially suspicious area is present;

if a potentially suspicious area is present, performing an image processing method on the area comprising the steps of:

enhancing the area in the noise-suppressed image; and further enhancing the potentially suspicious area with the use of a filter having sensitivity to a shape feature of a lung nodule and having relative insensitivity to an overlapping object; and segmenting the further enhanced potentially suspicious area with the use of adaptive clustering; and if no potentially suspicious area is present, determining that no lung nodules are present; and electronically transmitting the processed image and a determination as to the presence or absence of a lung nodule from the first site to the second site.

\* \* \* \* \*